United States Patent [19]

Kvakovszky et al.

[11] Patent Number: 5,241,098

[45] Date of Patent: Aug. 31, 1993

[54] METHOD FOR PREPARING A SALT OF 4-HYDROXYSTYRENE AND FOR PREPARING 4-TERTIARY-BUTOXYCARBONYLOXYSTYRENE THEREFROM

[75] Inventors: George Kvakovszky; James H. Rea; Michael T. Sheehan, Corpus Christi, all of Tex.; Brad L. Smith, Matthews, N.C.

[73] Assignee: Hoechst Celanese Corporation, Somerville, N.J.

[21] Appl. No.: 614,766

[22] Filed: Nov. 16, 1990

[51] Int. Cl.$^5$ .................... C07C 69/96; C07C 39/06
[52] U.S. Cl. ............................. 558/270; 568/780
[58] Field of Search .................. 558/270; 568/780

[56] References Cited

U.S. PATENT DOCUMENTS 4,491,628  1/1985  Hiroshi et al. .................. 430/176
5,087,772  2/1992  Sheehan et al. ................ 568/804

OTHER PUBLICATIONS

Carson et al, "Preparation of Cinylphenols and Isopropenylphenols", vol. 23, Apr. 1958, *J. Org. Chem.*

Fretchet et al, "Poly(p-tert-butoxycarbonyloxystyrene): A Convenient Precursor to p-Hydroxystyrene Resins", *Polymer*, 1983, p. 995.

*Primary Examiner*—Jose G. Dees
*Assistant Examiner*—Joseph Conrad, III
*Attorney, Agent, or Firm*—Donald R. Cassady; Jerome Rosenstock

[57] ABSTRACT

The present invention pertains to a method of forming a salt of 4-hydroxystyrene by reacting 4-acetoxystyrene with a suitable base in a suitable solvent system. Subsequently, or simultaneously, the salt of 4-hydroxystyrene can be reacted, preferably in situ, with di-tertiary-butyl-dicarbonate to form 4-tertiary-butoxycarbonyloxystyrene.

22 Claims, No Drawings

METHOD FOR PREPARING A SALT OF 4-HYDROXYSTYRENE AND FOR PREPARING 4-TERTIARY-BUTOXYCARBONYLOXYSTYRENE THEREFROM

BACKGROUND OF THE INVENTION

1. Field of the Invention

This invention relates to a method for preparing a salt of 4-hydroxystyrene by reacting 4-acetoxystyrene with a suitable base in a suitable solvent system; in addition, the method pertains to preparation of 4-tertiary-butoxycarbonyloxystyrene from the salt of 4-hydroxystyrene.

2. Description of the Prior Art

4-Hydroxystyrene is a well-known compound which is itself useful as a food flavoring substance and as an intermediate in the preparation of polymers and copolymers useful in coatings, electronic applications, ion exchange resins, photoresists, etc.

Although there are several ways to prepare 4-hydroxystyrene these known methods are not commercially feasible in the further utilization of 4-hydroxystyrene, such as for example for use in the preparation of a photoresist intermediate such as 4-tertiary-butoxycarbonyloxystyrene. The reason for this is that the 4-hydroxystyrene itself is difficult to isolate, in that it (1) readily decomposes, (2) is toxic via skin absorption, and (3) readily polymerizes. A preparation for 4-hydroxystyrene utilizing 4-acetoxystyrene is reported in a paper entitled "Preparation of Vinyl-phenols and Isopropyl-phenols", Corson et al., Volume 23, Apr. 1958 *J. Org. Chem.* In this preparation, 4-acetoxystyrene is saponified in an aqueous system with a large concentration of a soluble base, KOH, to produce an aqueous solution of the potassium salt of 4-hydroxystyrene which is neutralized with acid to precipitate 4-hydroxystyrene. As indicated above, the procedure is not practical or commercially feasible for production of large quantities of 4-hydroxystyrene because the 4-acetoxystyrene and/or the 4-hydroxystyrene is not very stable and readily polymerizes under the aqueous saponification conditions employed therein which involve high concentrations of soluble base, resulting in poor yields of 4-hydroxystyrene. A more efficient process for producing 4-hydroxystyrene from 4-acetoxystyrene is desired and needed. The instant invention provides a method whereby such ready polymerization of the 4-acetoxystyrene and/or the 4-hydroxystyrene in the formation of 4-hydroxystyrene is avoided.

4-Tertiary-butoxycarbonyloxystyrene is useful as an intermediate in the production of the photoresist material poly(4-tertiary-butoxycarbonyloxystyrene). The only published route to 4-tertiary-butoxycarbonyloxystyrene is reported by Frechet et al., Polymer, 1983, 995 and Ito et al., U.S. Pat. No. 4,491,628, which involves a Wittig reaction starting with p-hydroxybenzaldehyde. The formation of 4-tertiary-butoxycarbonyloxystyrene directly from p-hydroxystyrene has never been publicly reported, most likely due to the fact of the great instability of the 4-hydroxystyrene, as discussed above, and the difficulties most likely encountered thereby. These difficulties would lead one skilled in the art away from trying such synthesis using 4-hydroxystyrene even in the face of the synthesis of 4-tertiary-butoxycarbonyloxy-α-methylstyrene from 4-hydroxy-α-methylstyrene, as reported in U.S. Pat. No. 4,491,628. The reason for this is the fact that any α-substitution at the site of a carbon-carbon unsaturated bond lends great stability to that site and thereby resistance to polymerization, as compared to the unsubstituted site of the styrene unsaturation of 4-hydroxystyrene.

SUMMARY OF THE INVENTION

The present invention is directed to a method of preparing a relatively stable salt of 4-hydroxystyrene, which stable salt can be further utilized by direct reaction to form other compounds, such as 4-tertiary-butoxycarbonyloxystyrene, which is a photoresist intermediate. In one preferred embodiment of the invention, a salt of 4-hydroxystyrene is prepared by reacting 4-acetoxystyrene with a base in a suitable solvent system. Subsequently, this salt of 4-hydroxystyrene is reacted, preferably in situ, with di-tertiary-butyl-dicarbonate to form 4-tertiary-butoxycarbonyloxystyrene.

The salt of 4-hydroxystyrene can also be neutralized to provide 4-hydroxystyrene, thus providing a more stable precursor which can be converted to 4-hydroxystyrene as needed.

DETAILED DESCRIPTION

One preferred embodiment in accordance with the present invention relates to a method of synthesizing a salt of 4-hydroxystyrene of the formula

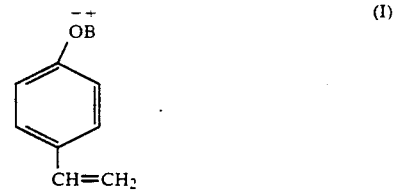
(I)

The synthesis of Compound I is made in the following manner. 4-Acetoxystyrene of the formula

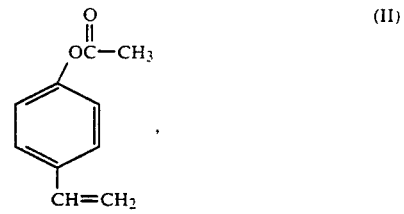
(II)

a known compound, which may be synthesized in accordance with the teachings of Corson et al., *J. Oro. Chem.* 23, 544 (1958), is selected. Compound II is then reacted with a suitable base of the formula BX (III), where B is the acidic or cationic moiety and X is basic or anionic moiety of the base, in a suitable solvent system to form the salt of Compound I.

A base, BX, of the kind useful in the above preferred embodiment is one which can hydrolyze or saponify Compound II to form the salt I directly. Such base includes inorganic bases such as metal hydroxides; preferably alkali metal hydroxides, e.g. KOH, NaOH, LiOH, etc.; preferrably KOH and NaOH; most preferrably KOH; an alkali metal alkoxide (an ionic organic base) such as $NaOCH_3$, $KOC(CH_3)_3$, etc. It is to be understood that a suitable mixture of the foregoing bases can be employed.

By a suitable solvent system is meant a solvent system comprising at least one suitable solvent. A suitable solvent is one in which the 4-acetoxystyrene (II) is soluble and the base (III) is only marginally soluble, forming a two-phase reaction system, so that homo and copolymerization of 4-hydroxystyrene, 4-hydroxystyrene salt and 4-acetoxystyrene (which occurs when base III is present in quantities exceeding that consumed in reaction with the 4-acetoxystyrene) is avoided. An example of this type of reaction system is the solvent ethyl acetate with the base potassium hydroxide. The suitable solvent selected will, of course, be dependent upon the base selected and the salt (Compound I) resulting therefrom which has to be soluble in such solvent. For the most common bases, e.g. sodium and potassium hydroxide, etc. some suitable solvents in which Compound I is soluble include ethylacetate, methylacetate, butylacetate, toluene, and tetrahydrofuran.

The base (III) can be mixed directly with the suitable solvent or can be dissolved in a second solvent which may or may not be miscible with the suitable solvent, provided that a suitable two-phase reaction system results.

The base, BX, is reacted with Compound II in amounts sufficient to fully saponify Compound II. Typically the molar ratio of BX to Compound II is in the range of about 0.8 to about 3.0 moles of BX to one mole of Compound II for suitable reaction systems, such as ethylacetate and potassium hydroxide.

Compound II is reacted with BX typically at a temperature of from about 0° C. to about 125° C., at a pressure ranging from about 1.0 to about 10.0 atmospheres and at a time period ranging from about 30 minutes to about 8.0 hours.

It has surprisingly been found that unlike conventional saponification of Compound II, in a miscible aqueous solvent system, the two-phase reaction system of the instant invention leads to good yields of Compound I without an inordinate amount of polymerization of either Compound II, 4-hydroxystyrene or resultant Compound I. Accordingly, it is critical that the reaction be conducted under reaction conditions whereby the concentration of base BX is kept low during reaction and this can be accomplished by the resultant two-phase system described.

The resultant salt, Compound I, may be neutralized, such as for example by the addition of acetic acid to form, essentially polymer free, 4-hydroxystyrene which may then be concentrated by cold filtration and freeze-dried under vacuum. This isolated 4-hydroxystyrene should be stored below 0° C. due its thermal instability above this temperature.

The salt of 4-hydroxystyrene (Compound I) can be used in the preparation of 4-tertiarybutoxycarbonyloxystyrene the formula

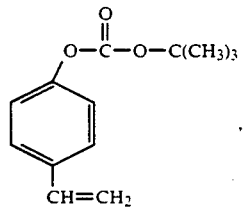

(IV)

which is useful as a starting material in the preparation of polymers for use in photoresists. Heretofore, there has been no published method of producing Compound IV directly from 4-hydroxystyrene, due to the unstable nature of 4-hydroxystyrene, the ease of polymerization thereof, the fact that it easily decomposes, and the fact that it is very hygroscopic and very difficult to dry.

It has now been discovered that Compound IV can be synthesized from Compound I which has been formed as described above, followed by an in situ reaction or treatment of Compound I to form Compound IV. Compound I is formed, as described above, by reaction of Compound II with the base, BX, (III) e.g. KOH, in the presence of the suitable solvent, e.g. ethylacetate, at a suitable temperature, e.g. 30° C.

Compound I, in turn is reacted in situ with di-tertiarybutyldicarbonate, of the formula

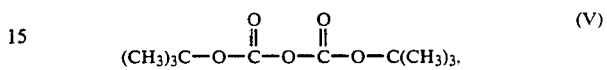

to form Compound IV. Typically this reaction is conducted at a temperature of 0° to 40° C. for 0.5 to 4.0 hours.

Surprisingly it has been found that Compound IV is readily formed in good yields without evidence of large polymerization or decomposition products resulting from either Compound II or Compound I. It is hypothesized that this result occurs because the synthesis of salt IV occurs directly under conditions which avoid high concentrations of the base BX.

In a second preferred embodiment for the formation of Compound IV, Compound I is made by using 4-hydroxystyrene synthesized by the method described in a U.S. patent application by Michael T. Sheehan et al., entitled "A METHOD FOR PREPARING 4-HYDROXYSTYRENE", which appliction is being filed simultaneously with this application and which is incorporated by reference hereinto in its entirety. The 4-hydroxystyrene is then reacted with a base to form Compound I.

In the Sheehan et al. method, the 4-acetoxystyrene (Compound II) is reacted, via a transesterification, with a suitable alcohol in the presence of a catalytic amount of a base to form 4-hydroxystyrene. The 4-hydroxystyrene is subsequently reacted with a base according to the present invention, to produce Compound I. Compound I is then converted to Compound IV as described above.

When Compound I is produced by reaction of a base with 4-hydroxystyrene produced by the transesterification route, suitable alcohol for the transesterification reaction is an alcohol or a suitable mixture of alcohols having the formula ROH (VI), where R is lower alkyl, where the term "lower" means the group it is describing contains from 1 to 6 carbon atoms; the term "alkyl" refers to a straight or branched chain hydroxycarbon containing no unsaturation, e.g. methyl, ethyl, propyl, isopropyl, butyl, 2-butyl, n-pentyl, n-hexyl, etc.

The lower the molecular weight and the less branching of the alkyl group, R, the better is the alcohol in terms of the yield of the target Compound I. Preferred alcohols (Compound VI) are methanol, ethanol, propanol and isopropanol. A most preferred Compound VI or suitable alcohol is methanol and ethanol. It is understood that a suitable mixture of the foregoing alcohols can be employed.

A base of the kind useful in the transesterification reaction includes inorganic bases such as metal hydroxides; preferably an alkali metal hydroxide, e.g. KOH, NaOH, LiOH, etc.; preferably KOH and NaOH; most preferably KOH; an alkali metal alkoxide such as NaOCH₃, KOC(CH₃)₃, etc.; inorganic carbonates, e.g. K₂CO₃; alkali organic acid salt, such as potassium acetate, etc.; a nitrogen base such as tri-loweralkylamines, e.g. trimethylamine, triethylamine, tripropylamine, etc. which is readily soluble in alcohol (VI). It is to be understood that a suitable mixture of the foregoing bases can be employed.

By a "catalytic amount" is meant an amount of base which will optimize the yield of Compound I, at the time and temperature selected to run the reaction, with a minimum amount of polymerization of Compound II. This catalytic amount can readily be determined for the suitable alcohol, suitable base, time and temperature selected, by one of ordinary skill in the art without an undue amount of experimentation in the light of the disclosure contained herein. Typically, a catalytic amount of a suitable base, e.g. KOH, ranges from a mole percent of the suitable base to Compound II of from about 1.5 mole percent to about 3.6 mole percent.

Upon reaction of Compound II with a suitable alcohol, Compound VI, e.g. methanol, in the presence of the catalytic amount of the suitable base, e.g. about 0.5 to about 3.0 mole percent of KOH, 4-hydroxystyrene forms in good yields, with a minimum amount of polymerization of Compound II. In addition to 4-hydroxystyrene, an acetate ester VII of the formula

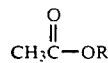
(VII)

forms. The resultant reaction accordingly is a transesterification type reaction. Transesterification reactions typically are catalyzed with acid and usually proceed very well in the presence of acid. It has been found that attempts to react Compound II with a suitable alcohol, Compound VI, in the presence of acid leads to polymerization of 4-hydroxystyrene and/or Compound II rather than formation of target 4-hydroxystyrene. Accordingly, the utilization of the suitable base is critical. It is also critical that only the catalytic amount of suitable base be employed. For example, if large concentrations of the suitable base, e.g. KOH, are employed, such as those concentrations typically employed in aqueous saponification, then the salt of 4-hydroxystyrene, Compound I, is formed, however a great degree of undesirable polymerization occurs.

The concentration of the suitable alcohol, Compound VI, to Compound II, during the reaction therebetween, is in excess of a 1 to 1 molar ratio, typically ranging from about 10 to about 20 times in excess of Compound VI to Compound II.

The reaction may be conducted at a temperature typically ranging from about 25° C. to reflux, for a period of time sufficient to complete the reaction. In this regard, the higher the temperature the shorter the reaction time that is necessary. In addition, the greater the catalytic amount employed at a particular temperature the less will be the reaction time. For example with about 1.5 molar percent of the suitable base, e.g. KOH, at reflux temperature e.g. 65° C. for methanol, the reaction time is typically about 4 to about 5 hours to get complete reaction of Compound II, whereas at a catalytic amount of about 3.0 mole percent of the suitable base, e.g. KOH, at the same reflux temperature, the reaction time is typically about 1 to about 2.5 hours to get essentially complete reaction of Compound II.

The acetate ester, Compound VII, e.g. methyl acetate, may be removed during the course of the reaction to drive the reaction and the formation of 4-hydroxystyrene to completion. Additionally, resultant salt, e.g. the potassium salt form of Compound I, present in the excess suitable alcohol, is neutralized, such as for example by the addition of acetic acid, whereafter the excess alcohol (Compound VI) is removed from the reaction container, by any conventional manner, as for example by evaporation under reduced pressure; followed by recrystallization of 4-hydroxystyrene from a suitable solvent, such as toluene, benzene and mixtures of aromatic hydrocarbons, e.g. benzene, toluene, etc., with a paraffin, such as hexane, petroleum ether, etc., at a temperature ranging from −78° C. to 25° C.. In addition, 4-hydroxystyrene can be redissolved in a suitable solvent such as an alcohol, e.g. methanol, and reprecipitated from solution by the addition of water to obtain isolated 4-hydroxystyrene.

The resultant 4-hydroxystyrene can, after conversion to a salt, be used in the preparation of 4-tertiarybutoxycarbonyloxystyrene, Compound IV. However, due to the instability of 4-hydroxystyrene, is is not practical to isolate this compound and use it as a starting material for Compound IV.

It has now been discovered that Compound IV can be synthesized from 4-hydroxystyrene by a "one-pot" or in situ reaction of 4-hydroxystyrene to form Compound IV. The 4-hydroxystyrene is formed, as described above, by reaction of Compound II with Compound VI in the presence of the catalytic amount of suitable base at a suitable temperature, e.g. 65° C.. The resultant 4-hydroxystyrene is not isolated but is further reacted in situ with an equimolar amount or concentration of the suitable base III to form the salt

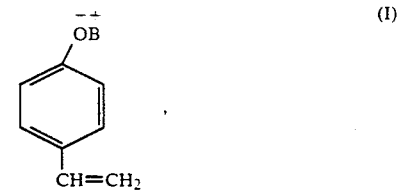
(I)

where B is the cationic moiety of the suitable base. This salt formation is typically carried out at a temperature of about −10° C. to about 25° C. for a time period sufficient to form Compound I (typically about 10 to 20 minutes).

Compound I, in turn can be reacted in situ with the di-tertiary-butyl-dicarbonate, to form Compound IV. Typically this reaction is conducted at a temperature of 0° C. to 40° C. for 0.5 to 4 hours.

Surprisingly, it has been found that Compound IV is readily formed and that polymerization of 4-hydroxystyrene is minimized. It is hypothesized that this surprising result occurs because 4-hydroxystyrene is not isolated. This therefore leads to good yields, of at least 50%, (typically 70% to 85%) of Compound IV.

In a third preferred embodiment of the present invention, a method which is a hybrid of the first two preferred embodiments is used to produce, ultimately, 4-tertiarybutoxycarbonyloxystyrene (Compound IV). In this third embodiment, 4-acetoxystyrene (Compound II) is again reacted with a base, however the solvent system in which the reaction takes place is one in which solvents of the kind described as "suitable solvents" in the first preferred embodiment herein (for example, but not limited to ethylacetate, methylacetate butylacetate, toluene, and tetrahydrofuran) are used in combination with alcohols of the kind described in the second preferred embodiment herein (for example, but not limited to, methanol, ethanol, propanol, and isopropanol). The alcohols are typically miscible with the "suitable solvents" and therefore are available to react with Compound II, via a transesterification reaction, to produce 4-hydroxystyrene. Thus, a portion of the salt of 4-hydroxystyrene (Compound I) is produced by direct reaction of the base with Compound II, while another portion of Compound I is produced by transesterification of Compound II to 4-hydroxystyrene with subsequent reaction with the base to form Compound I.

In any case, it is important that the amount of base present during the reaction process be carefully controlled so the undesired polymerization products previously described do not form. In addition, if Compound I is immediately converted to Compound IV this also helps avoid the formation of the polymerization products. With these considerations in mind, the reaction to convert compound II to Compound IV is starved for the base by adding such base continually (or in small quantities) during the reaction. In addition, the di-tertiary-butyl-dicarbonate (Compound V) is also typically added continually during the reaction. There is some evidence that Compound V reacts with the base and therefore a slight excess of Compound V is used, in combination with its continual addition, to compensate for this potential side reaction.

Bases useful in this third embodiment of the invention include organic bases such as metal hydroxides, preferably alkali metal hydroxides, e.g. KOH, NaOH, LiOH, etc., preferably KOH and NaOH, most preferably KOH; and alkali metal alkoxides (ionic organic base) such as NaOCH$_3$, KOC (CH$_3$)$_3$, etc. and combinations thereof.

The reaction conditions used are those equivalent to the reaction conditions described in the first preferred embodiment herein.

The yields of 4-tertiarybutoxycarbonyloxystyrene (IV) achieved range from about 80% to 98+% based on Compound II starting material.

A particular advantage of this hybrid method is that less of the very expensive Compound V is consumed.

Presented below are the results of several experiments which illustrate the practice of preferred embodiments of the subject invention.

EXAMPLES

Examples 1-5 are in support of the first embodiment of the invention as previously described, wherein a relatively stable salt of 4-hydroxystyrene is prepared by reacting 4-acetoxystyrene with a base in a "suitable solvent" system. The salt of 4-hydroxystyrene can then be reacted with tertiarybutyldicarbonate to form 4-tertiarybutoxy- carbonyloxystyrene.

Example 1

To a solution of 100 g 4-acetoxystyrene in 506 g ethyl acetate, which solution was under one atmosphere of pressure and a nitrogen purge, was charged, in one lot, 51 g of pulverized potassium hydroxide pellets. Molten di-tertiary-butyl-dicarbonate, 189 g, was added, in small increments, over a period of 33 minutes. The contents of the vessel were stirred at 25° C., with ice-bath cooling, for an additional 2.3 hours. After aqueous wash the organic phase, 628 g, was analyzed by gas chromatography (GC) and was found to contain 49 g of unchanged 4-acetoxystyrene and 32 (24% yield) of 4-tertiary-butoxycarbonyloxystyrene (IV).

Example 2

To a solution of 101 g 4-acetoxystyrene in 506 g ethyl acetate, which solution was at atmospheric pressure under a nitrogen purge, was charged, in one lot, 87 g pulverized potassium hydroxide. The reaction was stirred at 23° C. with cooling by ice-bath for a period of about 4 hours. Then 191 g di-tertiary-butyl-dicarbonate was charged over a period of 37 minutes and the reaction was stirred at 23° C. for an additional hour. After aqueous wash of the reaction product, GC analysis showed that the organic phase contained 103.5 g (77% yield) 4-tertiary-butoxycarbonyloxystyrene (IV).

Example 3

To a solution of 76 g 4-acetoxystyrene in 380 g ethyl acetate, which solution was at atmospheric pressure under a nitrogen purge, was added, in one lot, 65 g of pulverized potassium hydroxide. The reaction was stirred at 12° C. with ice-bath cooling. After 2 hours the reaction product was washed with 146 g of water. The organic phase was separated and 133 g molten di-tertiary-butyl-dicarbonate was added over a period of 37 minutes. After an additional 2 hours of reaction, the reaction solution was analyzed by GC and was found to contain 84.4 g (84% yield) 4-tertiary-butoxycarbonyloxystyrene (IV).

Example 4

To a solution of 40 g 4-acetoxystyrene in 101 g ethyl acetate, which solution was under atmospheric pressure and a nitrogen purge, was charged, in one lot, 28 g of potassium hydroxide pellets. A reaction was carried out for about 5 hours at 24° C.. Then molten di-tertiary-butyl-dicarbonate, 62 g, was introduced over a period of 20 minutes. After 2 hours the thick slurry was diluted with 101 g ethyl acetate and stirred for an additional hour. After aqueous washing the solvent was stripped on a rotary evaporator and the residual oil was charged with 0.04 g phenothiazine. Distillation at 0.1 mm Hg gave 45 g (84% yield) 4-tertiary-butoxycarbonyloxystyrene (IV).

Example 5

To a solution of 101 g 4-acetoxystyrene in 500 g ethyl acetate, which solution was under atmospheric pressure and nitrogen purge, was added 85 g of pulverized potassium hydroxide, added in portions, so as to maintain the reaction temperature at 40° C.. After 3 hours of reaction, 191 g of molten di-tertiary-butyl-dicarbonate was added, over a period of 37 minutes, and the reaction was stirred at 40° C. for an additional 1.3 hours. After aqueous washing of the reaction product, the organic layer was analyzed by G.C. The yield of 4-tertiary-butoxycarbonyloxystyrene (IV) was 95 g (71% yield).

Examples 6–7 are in support of the second embodiment of the invention as previously described, wherein 4-hydroxystyrene is produced by the transesterification of 4-acetoxystyrene in the presence of a catalytic amount of a base, followed by reaction of the 4-hydroxystyrene is then reacted with a base to form the salt of 4-hydroxystyrene. The salt of 4-hydroxystyrene can then be reacted with di-tertiary-butyl-dicarbonate to form 4-tertiarybutoxycarbonyloxystyrene.

Example 6

A solution comprising 2.4 g of potassium hydroxide, 201 g 4-acetoxystyrene and 500 g of methanol was heated at reflux for 2.2 hours. The reaction was cooled to 12° C. and 64 g potassium hydroxide pellets were added over a period of 10 minutes. After warming to 25° C., 314 g di-tertiary-butyl-dicarbonate was introduced over a period of one hour. After an additional 2.3 hours of reaction time, the reaction slurry was washed with water and extracted with ethyl acetate. The ethyl acetate was stripped from the extraction mixture using a rotary evaporator, and the residual oil was charged with 0.26 g phenothiazine inhibitor. Distillation at 0.1 mm Hg yielded 227.2 g (85% yield) 4-tertiary-butoxycarbonyloxystyrene (IV).

Example 7

A solution comprising 0.49 g potassium hydroxide, 40 g of 4-acetoxystyrene, and 100 g of absolute ethanol was refluxed for 4 hours. The reaction solution was cooled to 28° C. and 13 g potassium hydroxide pellets were added over a period of 10 minutes. After an additional 30 minutes of reaction, 64 g di-tertiary-butyl-dicarbonate was charged portionwise over 20 minutes and the reaction was stirred for an additional hour at 28° C.. After aqueous washing, the reaction product was extracted with ethyl acetate. The ethyl acetate was stripped from the extraction mixture on a rotary evaporator and the residual oil was charged with 0.07 g phenothiazine. Distillation at 0.1 mm Hg gave 34.2 (64%) 4-tertiary-butoxycarbonyloxystyrene (IV).

Examples 8–10, which each include multiple experiments, are in support of the third embodiment of the invention which pertains to a hybrid method of forming 4-tertiarybutoxycarbonyloxystyrene.

Example 8

A solution of 85 g (1.3 moles) of potassium hydroxide in 161 g of methanol was added in periodic additions along with 229 g (1.0 moles) of di-t-butyl dicarbonate to a stirred solution of 101 g (0.65 moles) of 4-acetoxystyrene in 505 g of ethyl acetate over a period of about 40 minutes. The reagents were added concurrently in approximately equal aliquots while the reaction mixture was kept at 25° C. with an ice bath. After an additional 2 hours of reaction at 25° C., the reaction slurry was washed well with water to remove solids. The volatile components of the organic layer were stripped under vacuum to give 148 g (83% crude yield) of 4-t-butoxycarbonyloxystyrene. Vacuum distillation afforded 87 g (65% yield) of pure product, b.p. 111° C./0.25 mm.

Example 9

A solution of 751 g (4.6 moles) of 4-acetoxystyrene in 3767 g of ethyl acetate was charged to a 12-liter three-necked flask equipped with a mechanical stirrer, condenser, and ice-bath. A solution of 634 g (0.8 moles) of potassium hydroxide in 1197 g of methanol, and 1685 g (7.6 moles) of molten di-tert-butyl dicarbonate was added in small poritons to the stirred reaction mixture, over a period of 1 hour 20 minutes. The reaction temperature was maintained at 25° C. throughout the addition. The contents of the vessel were stirred an additional 1.4 hours at 25° C. The reaction slurry was washed twice with 4-liter portions of deionized water. The organic layer was vacuum stripped at 35° C. and 50 mm Hg until most of the solvent had been removed. The residue was further stripped at 75° C. and 1.5 mm Hg. The residual oil, 1015 g (99.5% conversion and 82% yield, based on 4-acetoxystyrene) was vacuum distilled to yield pure t-botoxycarbonyloxystyrene (TBSM). Yields observed in multiple experiments, employing the above procedure are shown below. The method is not yet optimized in terms of all of the variables, which variables may have differed slightly from batch to batch, accounting for the range in yield.

| Batch No. | % Yield TBSM |
| --- | --- |
| 1 | 86.7 |
| 2 | 90.0 |
| 3 | 90.0 |
| 4 | 97.1 |
| 5 | 81.3 |
| 7 | 90.8 |
| 8 | 92.1 |
| 9 | 96.1 |

Example 11

The reaction described in Example 11 was repeated, except the 10% less di-tert-butyl dicarbonate (6.8 moles) was used. The yields of tert-butoxycarbonyloxystyrene (TBSM), 4-acetoxystyrene basis, observed in multiple runs, employing this procedure, are shown below.

| Batch No. | % Yield TBSM |
| --- | --- |
| 1 | 98.1 |
| 2 | 95.2 |
| 3 | 98.4 |
| 4 | 94.3 |
| 5 | 97.9 |
| 6 | 97.3 |
| 7 | 94.7 |
| 8 | 92.3 |
| 9 | 97.2 |

We claim:

1. A method for preparing a salt of 4-hydroxystyrene, which comprises:
   reacting 4-acetoxystyrene with a base in a two-phase reaction system comprising said 4-acetoxystyrene, said base and a solvent in which 4-acetoxystyrene is soluble and said base is only marginally soluble, to form said salt of 4-hydroxystyrene.

2. A method for preparing 4-hydroxystyrene from a salt of 4-hydroxystyrene prepared by the method of claim 1 comprising neutralizing said salt to form 4-hydroxystyrene.

3. The method as defined in claim 1 wherein said base is one selected from the group consisting of an inorganic metal hydroxide, an ionic organic base, a non-ionic organic base and a suitable mixture of any of the foregoing.

4. A method for preparing 4-tertiarybutoxycarbonyloxystyrene from a salt of 4-hydroxystyrene prepared by the method of claim 1 comprising reacting, said salt with ditertiarybutyldicarbonate, without isolation of said salt from essentially the reaction medium of claim 1, to form 4-tertiarybutoxycarbonyloxystyrene.

5. A method for preparing 4-tertiarybutoxycarbonyloxystyrene which comprises:
   (a) forming a solid-liquid phase reaction system comprising at least 4-acetoxystyrene, a first portion of a base in said liquid phase, and a solvent in which 4-acetoxystyrene is soluble and said base is only marginally soluble, with the remainder of said base in said solid phase;

(b) reacting said 4-acetoxystyrene with said first portion of a base to form a salt of 4-hydroxystyrene; and (c) reacting ditertiarybutyldicarbonate with said salt of 4-hydroxystyrene to form 4-tertiarybutoxycarbonyloxystyrene.

6. The method as defined in claim 5 wherein said base is one selected from the group consisting of an inorganic metal hydroxide, an ionic organic base, a nonionic organic base and a suitable mixture of any of the foregoing.

7. A method for preparing a salt of 4-hydroxystyrene, which comprises:

(a) reacting 4-acetoxystyrene with a suitable alcohol in the presence of a catalytic amount of a base to transesterify said alcohol and said 4-acetoxystyrene, forming a product mixture comprising 4-hydroxystyrene; and (b) adding to said product mixture an additional amount of a base to convert said 4-hydroxystyrene to a salt thereof.

8. A method for preparing 4-tertiarybutoxycarbonyloxystyrene from a salt of 4-hydroxystyrene prepared by the method of claim 7 which further comprises:

(c) reacting said salt, without isolation of said salt from essentially the reaction medium of step (b), with ditertiarybutyldicarbonate to form 4-tertiarybutoxycarbonyloxystyrene.

9. The method as defined in claim 8 wherein said catalytic amount is from about 0.5 molar percent to about 3.0 molar percent based upon the concentration of said base to said 4-acetoxystyrene.

10. The method as defined in claim 8 wherein step (a) said alcohol is methanol, said base is KOH and said reaction is carried out at a temperature of about 25° C. to about 65° C. for about 1 to about 6 hours.

11. The method as defined in claim 8 wherein step (b) said base is selected from the group consisting of potassium hydroxide, sodium hydroxide, lithium hydroxide, $K_2CO_3$, triethylamine, $KOC(CH_3)_3$, $NaOCH_3$, $KOCH_3$, tripropylamine, potassium-tertiarybutoxide and any suitable mixture of the foregoing.

12. The method as defined in claim 8 wherein said suitable alcohol is one having the formula ROH where R is lower alkyl.

13. The method as defined in claim 12 wherein in step (c) said reaction is conducted at a temperature of about 0° C. to about 30° C. for a time period of about 0.5 hour to about 4 hours.

14. The method as defined in claim 12 wherein said alcohol is one selected from the group consisting of methanol, ethanol, propanol, isopropanol and any suitable mixture of the foregoing.

15. The method as defined in claim 14 wherein said alcohol is selected from the group consisting of methanol, ethanol and a mixture of the foregoing.

16. The method as defined in claim 15 wherein said base is selected from the group consisting of potassium hydroxide, sodium hydroxide, lithium hydroxide, $K_2CO_3$, triethylamine, $KOC(CH_3)_3$, $NaOCH_3$, $KOCH_3$, tripropylamine, potassium-tertiary butoxide and any suitable mixture of the foregoing.

17. The method as defined in claim 16 wherein said base is KOH.

18. A method for preparing 4-tertiarybutoxycarbonyloxystyrene, which comprises:

(a) preparing a solution comprising 4-acetoxystyrene and at least one solvent in which 4-acetoxystyrene is soluble; and, (b) contacting said solution with an alcohol, a base, and with di-tertiarybutyldicarbonate to form 4-tertiarybutoxycarbonyloxystyrene, wherein said base is only marginally soluble in said solvent.

19. The method of claim 18, wherein said base is added periodically in small quantities or continuously throughout said contacting time period.

20. The method of claim 19, wherein said base is mixed with said alcohol and the mixture is added periodically.

21. The method of claim 20, wherein said di-tertiarybutyldi-carbonate is added periodically in small quantities or continuously throughout said contacting time period.

22. The method of claim 19, wherein said di-tertiarybutyldicarbonate is added periodically in small quantities or continuously throughout said contacting time period.

* * * * *